United States Patent [19]

Herweh et al.

[11] 4,053,538
[45] Oct. 11, 1977

[54] BLOCK POLYMERS FROM ISOCYANURATE-BASED POLYESTERS AND CONVENTIONAL POLYESTER SEGMENTS

[75] Inventors: John E. Herweh, Lancaster; William Y. Whitmore, Hellam, both of Pa.

[73] Assignee: Armstrong Cork Company, Lancaster, Pa.

[21] Appl. No.: 675,453

[22] Filed: Apr. 9, 1976

[51] Int. Cl.$^2$ .................. C08L 67/00; C08G 63/68
[52] U.S. Cl. .......................... 260/860; 260/75 N
[58] Field of Search ........................... 260/860, 75 N

[56] References Cited

U.S. PATENT DOCUMENTS

| | | | |
|---|---|---|---|
| 3,407,200 | 10/1968 | Little et al. | 260/75 N X |
| 3,651,014 | 3/1972 | Witsiepe | 260/75 R |
| 3,784,520 | 1/1974 | Hoeschele | 260/860 X |
| 3,962,188 | 6/1976 | Kauffman | 260/75 N |
| 3,962,191 | 6/1976 | Kauffman | 260/75 N |
| 3,962,192 | 6/1976 | Kauffman | 260/75 N |
| 3,968,183 | 7/1976 | Hayashi et al. | 260/860 |

OTHER PUBLICATIONS

Deanin, *Polymer Structure Properties and Applications*, Cahners Books, Boston, Mass. (1972), pp. 53-55.
Sweeting, *The Science and Technology of Polymer Films*, Interscience Publishers, N. Y. (1968), pp. 28-29.

*Primary Examiner*—Howard E. Schain
*Assistant Examiner*—W. C. Danison, Jr.
*Attorney, Agent, or Firm*—Richard J. Hammond

[57] ABSTRACT

A substantially linear segmented copolymer of the formula $(MX)_n$ where $n$ is an integer greater than 0 and M is a bivalent organic radical segment of the formula

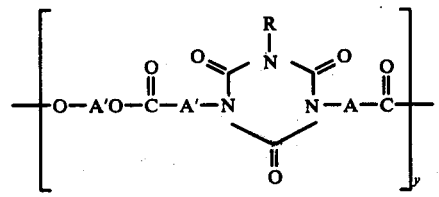

wherein R is hydrogen, $C_1$ to $C_4$ alkyl, aryl, or $C_1$ to $C_4$ alkyl substituted aryl; A is $C_1$ to $C_4$ alkylene; A' is $C_1$ to $C_4$ alkylene the same or different than A, phenylene or alkyl substituted phenylene; and $y$ is an integer greater than 0; and X is a bivalent organic radical segment of the formula

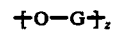

wherein G is a long chain radical segment of recurring linkages selected from the group consisting of ester and ether; and $z$ is an integer greater than 0 the same or different than $y$.

8 Claims, No Drawings

BLOCK POLYMERS FROM ISOCYANURATE-BASED POLYESTERS AND CONVENTIONAL POLYESTER SEGMENTS

BACKGROUND OF THE INVENTION

1. Field of the Invention

This invention relates to a new class of linear nitrogen heterocycle-containing copolymers and especially to those elastomers composed of block copolymers having alternating "soft" and "hard" segments in their internal structure with the "hard" segment being derived from a polymer having a majority of isocyanurate groups.

2. Description of the Prior Art

Isocyanurate compositions, such as those described in U.S. Pat. No. 3,407,200, are known as intermediates for the preparation of a variety of synthetic polymers useful as fibers, filaments, and the like. The materials prepared from such isocyanurate compositions exhibit excellent properties such as strength and elasticity, which is valuable in the manufacture of various protective coatings, as well as rope, hawser, fishing line, and so forth.

It is well known that physical blends of chemically dissimilar polymers are incompatible, and when blended in an attempt to modify their properties, suffer a substantial phase separation (and a lack of clarity) as well as the general degradation of the mechanical properties. Improvements over the physically blended polymers have been obtained by random copolymerization of desired prepolymeric materials. Recently, it has been noted that further improvements over the random copolymers are obtained by introducing a certain degree of order into the polymeric chain. One method to accomplish such improvement is by the formation of block copolymers. These materials are primarily defined as polymeric chains comprising two or more polymer segments of different chemical composition attached end to end. The term block copolymer can also include copolymers where very short polymer segments are attached together. As a limiting case, a regularly alternating copolymer may also be considered as block copolymer. Block copolymers may also include those segments formed from polar and nonpolar, crystalline and amorphous, and elastomeric and nonelastomeric structures. In block copolymers of the thermoplastic elastomeric type, the copolymer comprises amorphous segments having a low $T_g$, e.g., "soft" segments, and segments of high $T_g$, e.g., "hard" segments. Of particular interest are those block copolymers which have as hard segments polymeric chains containing a majority of polyisocyanurate linkages.

SUMMARY OF THE INVENTION

It is an object of the present invention to provide new synthetic materials capable of being formed into shaped articles having improved thermal stability and tensil strength.

A further object of the present invention is to provide linear synthetic polymers which are particularly adapted to the preparation of free retardant coatings and filaments, including those having a high elastic recovery which do not require curing or cross-linking to alter their properties.

Still another object of the invention is to provide a linear segmented polymer from prepolymeric segments that are essentially incompatible prior to polymerization.

These and other objects of the present invention are accomplished by the preparation of a substantially linear segmented copolymer having the formula $(MX)_n$ where $n$ is an integer greater than 0 and M is an organic solvent bivalent radical segment of the formula

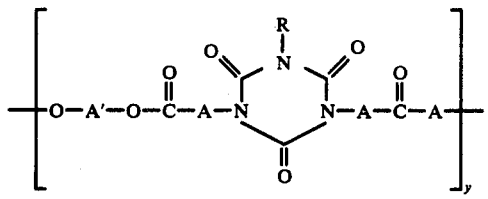

wherein R is hydrogen $C_1$ to $C_4$ alkyl, aryl or $C_1$ or $C_4$ alkyl substituted aryl, A is $C_1$ to $C_4$ alkylene; A' is $C_1$ to $C_4$ alkylene the same or different from A, phenylene or alkyl substituted phenylene; and $y$ is an integer greater than 0; and X is an organic radical segment of the formula

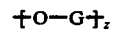

wherein G is a long chain radical segment of recurring linkages selected from the group consisting of ester and ether; and $z$ is an integer greater than 0 the same or different they $y$. The difference between the glass transition temperature of the organic bivalent material M and the organic bivalent radical X is from about 50° to about 200° C.

DESCRIPTION OF THE PREFERRED EMBODIMENTS

The novel linear segmented copolymers of the present invention can be obtained by any of the well-known generally practiced procedures for preparing polymers of the segmented type. Typically, the isocyanurate-bearing segment in its reactive form (difunctionally terminated) is joined to the segment of recurring linkages selected from the group consisting of ester and ether by the use of a coupling reagent. In the case of hydroxy-terminated segments, for example, such coupling reagent can be alkyl, aryl or mixed aralkyl diisocyanate, diacid chloride or dicarboxylic acid. Preferred in this case are the aliphatic diisocyanate, the aliphatic diacid chloride and the aliphatic dicarboxylic acid coupling reagents, allowing the "hard" segment/"soft" segment coupling to be carried out at moderate temperature in a solution phase polymerization. Since the amount of coupling reagent incorporated into the resultant copolymer is very small, the products of this polymerization are those block copolymers having the formula $(MN)_n$ where M is an isocyanurate-bearing segment of the formula

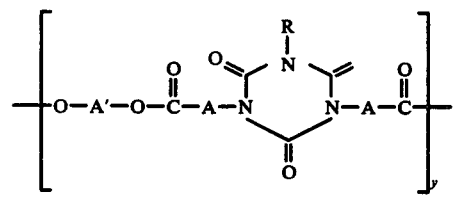

wherein R is hydrogen, $C_1$ to $C_4$ alkyl, aryl, or $C_1$ to $C_4$ alkyl substituted aryl, A is $C_1$ to $C_4$ alkylene; A' is $C_1$ to $C_4$ alkylene, phenylene or alkyl substituted phenylene;

and y is an integer greater than 0; and X is an organic radical segment of the formula

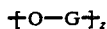

wherein G is a long chain radical segment of recurring linkages selected from the group consisting of ester and ether; and z is an integer greater than 0 the same or different than y. It has been found advantageous to have a difference between the glass transition temperature of the first segment and the glass transition temperature of the second segment of from about 50° to about 200° C.

The copolymers of this invention are comprised of "hard" segments, e.g., the M segment, and "soft" segments, e.g., the X segments, which are polymeric segments each having a molecular weight of at least 1,000. While it is preferable not to exceed a segment molecular weight in the case of both M and X of not over 20,000, the preferred molecular weight range for these "hard" and "soft" segments is from about 2,500 to about 5,000. It is particularly important in order to obtain the superior properties of the block copolymers of this invention to have a certain relationship between the glass transition temperatures ($T_g$) of the "hard" and "soft" segments. Thus, the difference between the $T_g$ of the "hard" segment and that of the "soft" segment may be as little as 50° C. and as much as 200° C., but should be preferably about 180° C, but not less than about 75° C. The most preferred difference in $T_g$ is from about 100° to 160° C. Differences larger than 200° C. are not desired since such differences give rise to difficulties in processing. If differences of less than 50° C. in $T_g$ exists between the "hard" and "soft" segments, then the advantage of having "hard" and "soft" blocks is entirely lost. Typically the $T_g$ of the "hard" segment is over 80° C., but may be less as long as the $T_g$ difference disclosed above is maintained.

As disclosed above, the "hard" segments of the segmented linear polymer of this invention are derived from polymeric radicals having an abundance of isocyanurate linkages. The preparation of difunctionally terminated isocyanurates useful in forming the "hard" segments of this invention have been described by Close, J. Amer. Chem. Soc. 75, 3617 (1953). The generally preparative procedure is according to the following equation

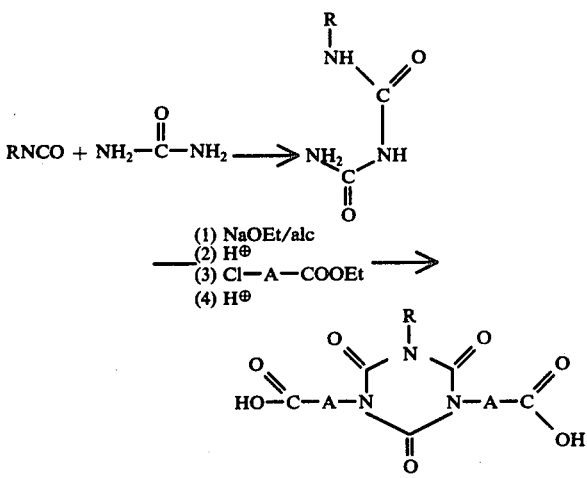

wherein R is hydrogen, alkyl such as methyl, ethyl, propyl, isopropyl, butyl, isobutyl, t-butyl, and pentyl, as well as branched pentyl and the like, aryl such as phenyl and the like, and alkyl substituted phenyl such as tolyl, xylyl, ethyl phenyl and so forth. Particularly preferred are those organic isocyanates where R is aryl, A is $C_1$ to $C_6$ alkylene such as methylene, ethylene, propylene, butylene, and the like. Isocyanurate prepolymer blocks, e.g., the "hard" segment, can be prepared by conventional classical chain extension techniques in which the carboxylic acids of the above-mentioned 1,3-biscarboxy-5-substituted isocyanurate is reacted with alcohols, amines, or thiols. For example, the biscarboxy isocyanurate can be reacted with alkylene diols such as ethylene glycol, propylene glycol, butylene glycol, hexamethylene-1,6-diol and decamethylene-1,10-diol, and the like to form prepolymeric hydroxy terminated polyester isocyanurates, e.g., the prepolymer "hard" segment of relatively high $T_g$. The relative quantities of the biscarboxylic acid and the diol can be varied somewhat to altar the molecular weight and the degree of esterification. However, it is preferable to employ an excess of diol in reaction with the biscarboxy isocyanurate. Very large molar excesses of diol, e.g., five times or over can be used, but an excess of twice the mole ratio of diol to isocyanurate is preferred. Mole ratios of 1:1 diol:isocyanurate or less lead to isocyanurate-bearing segments that are difficult to couple with the selected coupling reagents disclosed above and should be avoided unless other coupling reagents reactive to the isocyanurate-contributed carboxylic acid terminations are available.

Amines or thiol terminated prepolymeric amides or thioesters of the isocyanurates can also be formed by reaction of the 1,3-biscarboxy-5-substituted isocyanurate with alkylene diamines or dithiols.

A wide variety of other hydroxy-terminated materials can be used to react with the above-mentioned biscarboxy isocyanurate. Any suitable hydroxy-terminated polyester may be used such as are obtained, for example, from carboxylic acids and polyhydric alcohols.

Polyalkylene ether polyols may also be used such as the polymerization product of an alkylene oxide or an alkylene oxide with a polyhydric alcohol.

Any divalent organic radical having at least two reactive hydrogen atoms can be used as the "soft," X, segment of the copolymers of this invention. These include the above-disclosed glycols, and other hydroxy-terminated materials having the formula

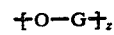

where G is a long chain radical segment of recurrent linkages selected from the group consisting of ester and ether and z is an integer greater than 0.

While divalent organic radicals are principally contemplated as the "soft" segment of this invention, those organic compounds that generate polyvalent radicals such as the polyols may also be used as component X in place of at least a part of the divalent segment. While there is a greater tendency to produce intractable polymer gels when the polyol contains such polyvalent radical component, it is preferable when using such polyol component as part of the "X" segment that the degree of functionality of such should not be so great that an intractable polymer is obtained. Such cross-linking aliphatic polyols often have from about 3 to 12, preferably from about 3 to 6, carbon atoms. When the polyol component used in making the "soft" segment of the copolymers of this invention contains cross-linking polyols, essentially the entire polyol may have at least about 3 hydroxy groups per molecule. Large amounts of such polyol or polyols of high functionality may preclude the dissolution and reaction of the polyol with the biscarboxy isocyanurate; therefore, it may be desirable to limit the hydroxy group used in the cross-linking polyol to up to about 10, preferably up to about 2, mole percent base on the total hydroxy content. Polyhydric polythioether polyols may also be used in this invention. These, for example, result from the condensation product of a thiodiglycol or the reaction product of a dihydric alcohol, such as disclosed above in the preparation of hydroxy-terminated polyesters with any other suitable thioether glycol. The scope of the invention is readily understood by referring to the following examples which are given for illustrative purposes only and should not be considered to represent the limits of the invention.

EXAMPLE 1

1,3-Bis(Carbethoxymethylene)-5-Phenylisocyanurate (2)

To 2000 ml of DMF was added disodium phenylisocyanurate (249 g, 1.0 mol) with stirring. Ethylchloroacetate (269.6 g, 2.2 mol) was added and the mixture heated at 75° C. for 8 hrs. The DMF was then removed on a rotary evaporator at reduced pressure leaving a white solid product. The residue was treated with 2000 ml of methylene chloride and washed with water. Evaporation, after drying over sodium sulfate, yielded crude 2. Recrystallization from $CCl_4$ yielded (90%) pure 2 (338 g, 0.9 mol): MP 154°–155° C.

Anal. Calcd. for $C_{17}H_{19}N_3O_7$: C, 54.11; H, 5.08; N, 11.14; Found: C, 53.97; H, 5.09; N, 11.30.

EXAMPLE 2

1,3-Bis(Carboxymethylene)-5-Phenylisocyanurate (3)

Diester 2 (50 g, 0.13 mol) was refluxed (100° C) with 400 ml of conc. HCl for 8 hrs. and upon cooling to 5° C., a solid precipitated from solution. The solid was collected by filtration and was recrystallized from 800 ml of water to yield (53%) of diacid 3 (29 g, 0.07 mol): mp 272°–273° C.

Anal. Calcd. for $C_{13}H_{11}N_3O_7$: C, 48.60, H, 3.45; N, 13.08; Found: C, 48.51; H, 3.46; N, 13.13.

EXAMPLE 3

1,3-Bis(2-Cyanoethyl)-5-Phenylisocyanurate (4)

To a solution of phenylisocyanurate (20.3 g, 0.1 mol) and 5 ml of Triton B (40% solution of benzyltrimethylammonium hydroxide in methanol) in 75 ml of DMF was added 25 ml of acrylonitrile (20.0 g, 0.38 mol). The reaction mixture was heated to 120° C. and held for 2 hrs. It was then cooled to room temperature and 5 ml of 6N HCl was added. The mixture was concentrated on a rotary evaporatory at reduced pressure yielding a viscous liquid. The viscous product as slurried with pentane and solidified upon cooling. The solid was recrystallized from ethanol yielding (64%) dinitrile 4 (19.8 g, 0.064 mol): mp 162°–164° C.

Anal. Calcd. for $C_{15}H_{13}N_5O_3$: C, 57,88; H, 4.21; N, 22.49; Found: C, 58.14; H, 4.10; N, 22.40.

EXAMPLE 4

1,3-Bis(2-Carboxyethyl)-5-Phenylisocyanurate (5)

A mixture of dinitrile 4 (200 g, 0.64 mol), conc. HCl (950 ml) and water (150 ml) was refluxed for 4 hrs., and then cooled to 0° C. The resulting precipitate was collected and recrystallized from water to yield (78%) diacid 5 (175 g, 0.50 mol): mp 174°–176° C.

Anal. Calcd. for $C_{15}H_{15}N_3O_7$: C, 51.58; H, 4.33; N, 12.03; Found: C, 51.38; H, 4.31; N, 11.99.

EXAMPLE 5

1,3-Bis(3-Carbethoxypropyl)-5-Phenylisocyanurate (6)

This diester was prepared in an analogous manner to that of diester 3, by alkylation of disodium phenylisocyanurate (124 g, 0.5 mol) with ethyl-3-chlorobutyrate (200 g, 1.3 mol) in DMF (1400 ml) at 75° C. for 8 hrs. The DMF was distilled off at reduced pressure and the residue treated with 1000 ml of methylene chloride, washed 3 times with 2000 ml of water, dried, and concentrated. The viscous product was distilled to yield (90%) diester 6 (180 g, .45 mol): bp of 228° C./.02 mm.

Anal. Calcd. for $C_{21}H_{27}N_3O_7$: C, 58.19; H, 6.28; N, 9.69; mol. wt. 433.5; Found: C, 58.19, H, 6.30; N, 9.68; mol. wt. 430.

EXAMPLE 6

1,3-Bis(3-Carboxypropyl)-5-Phenylisocyanurate (7)

A mixture of diester 6 (107 g, 0.25 mol) and conc. HCl (900 ml) were refluxed for 8 hrs. and allowed to cool. The solution was concentrated and the residue was recrystallized from methylene chloride to yield (76%) diacid 7 (70 g, 0.19 mol): mp 139°–140°.

Anal. Calcd. for $C_{17}H_{19}N_3O_7$: C, 54.11; H, 5.08; N, 11.14; Found: C, 54.16; H, 5.13; N, 11.05.

EXAMPLE 7

1,3-Bis(Carbethoxymethylene)-5-Methylisocyanurate (8)

To 1600 ml of DMF was added disodium methyl isocyanurate (324 g, 1.73 mol) with stirring. Ethylchloracetate (700 g, 5.73 mol) was added and the mixture heated at 70° C. for 5 hrs. The DMF was distilled off at reduced pressure and the viscous residue was treated with 1800 ml of methylene chloride. After washing with water and drying, the methylene chloride was evaporated to yield (60%) diester 8 (326 g, 1.03 mol): bp 180°/.05 mm; mp 63°–65° C.

Anal. Calcd. for $C_{12}H_{17}N_3O_7$: C, 45.71; H, 5.43; N, 13.33; Found: C, 45.94, H, 5.52; N, 13.29.

EXAMPLE 8

1,3-Bis(Carboxymethylene)-5-Methylisocyanurate (9)

A mixture of diester 8 (195 g, 0.62 mol), and conc. HCl (500 ml) was heated at reflux for 12 hrs. The solution was concentrated and the residue crystallized from water to yield (42%) diacid 9 (66 g, 0.25 mol): mp 235° C.

Anal. Calcd. for $C_8H_9N_3O_7$: C, 37.07; H, 3.50; N, 16.21; Found: C, 36.95; H, 3.42; 16.13.

EXAMPLE 9

1,3-Bis(Carboxymethylene)-5-Butylisocyanurate (10)

To 2500 ml of DMF was added disodium butylisocyanurate (404 g, 1.76 mol) with stirring. Ethylchloroacetate (720 g, 5.85 mol) was added and the mixture heated at 70° C. for 5 hrs. The DMF was distilled off at reduced pressure and the residue treated with 3500 ml of methylene chloride. After washing with water and drying, the methylene chloride was evaporated to yield (69%) diester 10 (433.5 g, 1.22 mol): bp 178° C./.02 mm; mp 42°–43° C.

Anal. Calcd. for $C_{15}H_{23}N_3O_7$: C, 50.42; H, 6.49; N, 11.76; Found: C, 50.45; H, 6.54; N, 11.68.

EXAMPLE 10

1,3-Bis(Carboxymethylene)-5-Butylisocyanurate (11)

A mixture of diester 10 (360 g, 1.02 mol) and conc. HCl (1500 ml) was heated at reflux for 12 hrs. The solution was concentrated and the residue was crystallised from water to yield (39%) diacid 11 (120 g, 0.40 mol): mp 145° C.

Anal. Calcd. for $C_{11}H_{15}N_3O_7$: C, 43.85; H, 5.02; N, 13.95; Found: C, 43.65; H, 4.98; N, 14.02.

All isocyanurate prepolymer blocks were prepared using similar melt polymerization techniques. (See for example, Sittig, M. Polyester Fikes Manufacturing, Noyes Data Corp., 1971.) This involved initial esterification or transesterification of the isocyanurate containing monomers with excess diol, followed by polycondensation under vacuum conditions. The following example is typical of the process employed.

EXAMPLE 11

Polymerization of 1,3-Bis(3-Carboxypropyl)-5-Phenylisocyanurate with Ethylene Glycol A mixture of 1,3-bis(3-carboxypropyl)-5-phenylisocyanurate (7) (20 g, 0.053 mol), ethylene glycol (.17 mol) and T-12 (0.5 g) was heated with stirring at 200° C. under nitrogen. The esterification process was continued for 8 hrs. with the liberated water continually removed by distillation. The pressure was then lowered over 30 min. to 0.01 mm and held for an additional 4–24 hrs. The pressure was then raised to atmospheric and the viscous polymer allowed to cool under nitrogen.

The substantially linear segmented copolymers of this invention were prepared using similar solution polymerization techniques. The following represents a typical coupling reaction with an organic diisocyanurate.

EXAMPLE 12

Block Copolymer from Polycaprolactone* and the Hydroxy-Terminated Polyester Based on Ethylene Glycol and 1,3-bis(Carboxymethylene)-5-Phenyl Isocyanurate A stirred mixture of the hydroxy-terminated polycaprolactone** (20 g, 10.1 mmol) and (20 g, 7.6 mmol) in 156 ml of dry, 1,2-DCE under $N_2$ was heated to reflux to effect solution. The reaction mixture temperature was left to drop to ca 80°; Hylene W (4.65 g, 17.7 mmol) and T-918 catalyst (0.0134 g) were quickly added. The resulting turbid pale yellow reaction mixture was heated at reflux for 17 hrs. Water (2.6 g) was then added and heating at reflux continued for 2 hrs.

*Union Carbide; molecular weight 1972, $T_g$ −70° C. (DSC) hydroxy number 56.95
**Among other copolymeric polyesters employed in the reaction with 1,3-biscarboxy isocyanurates was polyethylene terephthalate, Hooker Chemical, molecular weight 1592, $T_g$ +8 (DSC), hydroxy number 70.35

A series of block copolymers were synthesized using the same technique shown in Example 12. In the polymers produced in this manner, the isocyanurate segment (hard segment) is that from Example 11, e.g. the prepolymer formed by condensation of 1,3-bis(3-carboxypropyl)-5-phenylisocyanurate with ethylene glycol. The hydroxy-terminated polyester coupled with this "hard" segment was either polycaprolactone or polyethylene terephthalate as indicated. The coupling agent was the organo isocyanate, Hylene W. As indicated in Table I, the amount of isocyanurate "hard" segment and polyester "soft" segment was varied over the range 80:20 to 20:80 weight percent isocyanurate:polyester. Physical properties of the block copolymers A–E are shown in Table II. These block copolymers have Tg differentials within the scope of the present invention, e.g., from 200° to 50°. The copolymers all show acceptable compatibility (good clarity) and, depending on the weight percent isocyanurate segment, can vary from elastomers to hard plastic solids.

The turbid pale yellow viscous reaction mixture was concentrated to two-thirds volume on the rotary evap. at 60° (20 mm). Portions of the concentrate were coated (10 mil thick) on polypropylene release paper and the coated samples dried at 130° for 4 min. in an air-circulating oven. Further drying of the films was accomplished in vacuo (1.0 mm) at 100° for 2 hrs. The dried, clear, tough films were characterized by gpc, DSC, etc.

It will be apparent that many widely different embodiments of this invention may be made without departing from the spirit and scope thereof and, therefore, it is not intended to be limited in any way except as indicated in the appended claims.

Table I

Substantially Linear Segmented Copolymers Containing Isocyanurate-Bearing Segments

| % Isocyanurate[1] Polyester or Polyether Component[2] | A 80/20 g (mmol) | B 65/35 g (mmol) | C 57.3/42.7 g (mmol) | D 50/50 g (mmol) | E 20/80 g (mmol) | F 60/40 g (mmol) | G 50/50 g (mmol) |
|---|---|---|---|---|---|---|---|
| 1 | 28(10.6) | 26(9.9) | (26.4(10) | 20(7.6) | 8(3.0) | 13.8(5.2) | 11.5(4.35) |
| 2 | 7(3.6) | 14(7.1) | 19.7(10) | 20(10.1) | 32(16.2) | — | — |
| 3 | — | — | — | — | — | 9.2(5.78) | 11.5(7.21) |
| T-918 | 0.0116 | 0.0135 | 0.015 | 0.0134 | 0.0135 | 0.008 | 0.008 |
| Hylene W | 3.73(14.2) | 4.46(17.0) | 5.23(20) | 4.65(17.7) | 5.04(19.2) | 2.89(11.0) | 3.04(11.6) |
| $H_2O$ | 2.25 | 2.6 | 3.01 | 2.6 | 2.6 | 0.53 | 0.53 |

[1]Wt % isocyanurate-bearing segment/ester or ether bearing segment
[2]Component 1 - The product of Example 11
Component 2 - The polycaprolactone of Example 12
Component 3 - The polyethylene terephthalate of Example 12
T-918 - M&T Corp.
Hylene W - duPont, bis(4-isocyanatocyclohexyl) methane

Table II

Block Polymer Characterization and Properties

| Block Copolymer | Composition[a] | Tg's, °C[b] | $M_w$[c] | TGA[d] Inflection °C | % Elongation | Tensile Strength | Description of Material |
|---|---|---|---|---|---|---|---|
| A | 80/20 | −58,120 | — | — | — | — | hard, brittle, does not elongate clear |
| B | 65/35 | −57,81 | 31,700 | — | 60 | 3636 | hard, flexible, clear |
| C | 57.3/42.7 | −56,90 | 42,200 | 300 | 446 | 5105 | hard, flexible, clear |
| D | 50/50 | −54,95 | 29,400 | — | 307 | 3117 | hard, flexible, can be elongated, clear |
| E | 20/80 | −53,105 | — | — | 700 | 3098 | elastomeric, tough, can be elongated, clear |
| F | 60/40 | 14,87 | 28,300 | — | — | — | Somewhat flexible, hard, clear |
| G | 50/50 | 12,91 | 22,000 | — | — | — | similar to F |

[a]See Table I.
[b]Determined by DSC.
[c]Estimated from GPC data.
[d]In ry air, 6° per min.

What is claimed is:

1. A substantially linear segmented copolymer having the formula $(MX)_n$ wherein $n$ is an integer greater than 0 and M is a bivalent organic radical segment of the formula

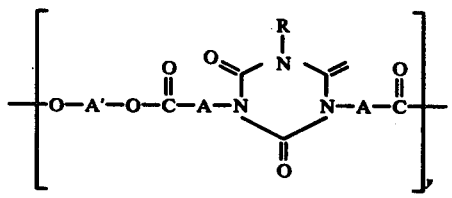

wherein R is hydrogen, $C_1$ to $C_4$ alkyl, aryl or $C_1$ to $C_4$ alkyl substituted aryl; A is $C_1$ to $C_4$ alkylene; A' is $C_1$ to $C_4$ alkylene the same or different from A, phenylene or alkyl substituted phenylene; and $y$ is an integer greater than 0, said segment M of molecular weight from 1,000 to 20,000; and X is a bivalent organic radical segment of the formula

wherein G is a long chain radical segment of recurring linkages selected from the group consisting of ester and ether; and $z$ is in integer greater than 0 the same or different than said segment X of molecular weight 1,000 to 20,000; wherein the difference between the glass transition temperature of said segment M and said segment X is from about 50° to about 200° C.

2. The copolymer of claim 1 wherein organic bivalent radical segments M and N are coupled with a coupling reagent selected from the group consisting of aliphatic diisocyanate, aliphatic diacid chloride, and aliphatic dicarboxylic acid.

3. The copolymer of claim 1 wherein M is

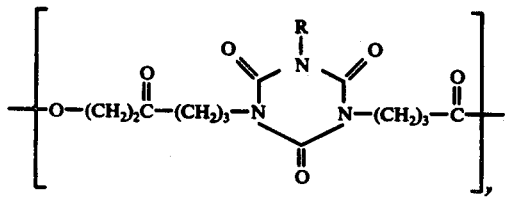

wherein R is hydrogen, $C_1$ to $C_4$ alkyl, aryl, or $C_1$ to $C_4$ alkyl substituted aryl; and $y$ is greater than 0 and X is selected from the group consisting of linear polyalkyllactone and polyalkylene phthalate.

4. The copolymer of claim 3 wherein R is phenyl and X is polycaprolacetone.

5. The copolymer of claim 1 wherein the ratio of M:X is from 2:8 to 8:2.

6. The copolymer of claim 3 wherein R is phenyl and X is polyethylene isophthalate.

7. A process for preparing a substantially linear segmented copolymer which comprises the steps of:

a. reacting a linear isocyanurate-containing polymer segment of the formula

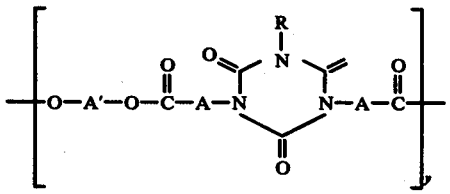

wherein R is hydrogen, $C_1$ to $C_4$ alkyl, aryl or $C_1$ to $C_4$ alkyl-substituted aryl; A is $C_1$ to $C_4$ alkylene; A' is $C_1$ to $C_4$ alkylene, the same or different from A, phenylene, or alkyl-substituted phenylene, and $y$ is an integer greater than 0, said linear isocyanurate-containing polymer having a molecular weight of 1,000 to 20,000 and terminally reactive groups selected from the group hydroxy, thiol and amine;

b. an organic polymer of the formula $—O—G]_z$ wherein G is a long chain radical segment of recurring linkages selected from the group ester and ether and $z$ is an integer greater than 0, the same or different than $y$, said organic radical segment having a molecular weight of 1,000 to 20,000 and at least two reactive hydrogens; and c. a coupling agent wherein the difference between the glass transition temperature of said linear isocyanurate-containing polymer segment and said organic polymer segment is from about 50° to about 200°.

8. The process of claim 7 wherein said substantially linear segmented copolymer comprises the ratio of said linear isocyanurate-containing polymer:said linear glycol of from 2:8 to 8:2.

* * * * *